United States Patent [19]
Simmons

[11] Patent Number: 5,224,941
[45] Date of Patent: * Jul. 6, 1993

[54] GARMENT WITH PROTECTIVE ELASTIC LEG DAMS

[75] Inventor: Frances B. Simmons, Westminster, S.C.

[73] Assignee: Gerber Childrenswear, Inc., Boston, Mass.

[*] Notice: The portion of the term of this patent subsequent to May 28, 2008 has been disclaimed.

[21] Appl. No.: 705,072

[22] Filed: May 24, 1991

Related U.S. Application Data

[63] Continuation of Ser. No. 337,574, Apr. 13, 1989, Pat. No. 5,019,067.

[51] Int. Cl.$^5$ .............................. A61F 13/15
[52] U.S. Cl. .................................. 604/385.2
[58] Field of Search .................. 604/385.1, 385.2; 2/78 B, 78 C, 400–402

[56] References Cited

U.S. PATENT DOCUMENTS

| | | | |
|---|---|---|---|
| 3,882,871 | 5/1975 | Taniguchi | 128/287 |
| 4,402,690 | 9/1983 | Redfern | 604/391 |
| 4,410,327 | 10/1983 | Baggaley | 604/391 |
| 4,427,408 | 1/1984 | Karami et al. | 604/393 |
| 4,475,912 | 10/1984 | Coates | 604/385 |
| 4,490,148 | 12/1984 | Beckeström | 604/385.2 |
| 4,537,591 | 8/1985 | Coates | 604/391 |
| 4,568,342 | 2/1986 | Davis | 604/391 |
| 4,608,047 | 8/1986 | Mattingly | 604/387 |
| 4,636,207 | 1/1987 | Buell | 604/370 |
| 4,680,030 | 7/1987 | Coates et al. | 604/391 |
| 4,687,478 | 8/1987 | Van Tilburg | 604/387 |
| 4,710,189 | 12/1987 | Lash | 604/385 |
| 4,743,246 | 5/1988 | Lawson | 604/385 |
| 4,808,178 | 2/1989 | Aziz et al. | 604/385.2 |
| 4,940,462 | 7/1990 | Salerno | 604/387 |
| 5,019,067 | 5/1991 | Simmons | 604/385.2 |

FOREIGN PATENT DOCUMENTS 0331018 9/1989 European Pat. Off. .

Primary Examiner—Randall L. Green
Assistant Examiner—D. Willse
Attorney, Agent, or Firm—Foley & Lardner

[57] ABSTRACT

The specification discloses a protective garment, specifically a diaper, whose body has opposed side portions folded inwardly towards one another, each along an arcuate fold line. An elastic strip in a partially stretched condition is folded over each fold line and secured in place to create a contoured protective garment having curved leg conforming side edges and inwardly projecting protective dams along each side of said garment.

6 Claims, 2 Drawing Sheets

GARMENT WITH PROTECTIVE ELASTIC LEG DAMS

This is a continuation application of U.S. Ser. No. 07/337,574 filed on Apr. 13, 1989, now U.S. Pat. No. 5,019,067, granted May 28, 1991.

BACKGROUND OF THE INVENTION

The present invention relates to protective garments such as diapers, diaper covers and diaper covering pants.

Diapers typically comprise a generally rectangular body made of an absorbant material. In some diapers, opposed side portions of the body are cut away along a generally arcuate leg line so that the diaper fits more neatly around the wearer's legs. Disposable diapers have been made with elastic strips secured in a stretched or partially stretched condition to the body generally adjacent the arcuate leg conforming side edges thereof, such that when the elastic is relaxed it helps to gather the diaper body in upon itself, thereby contouring the diaper, making it easier to fit to the wearer.

Contoured diaper covers or diaper covering pants have been similarly manufactured. Stretched or partially stretched elastic strips are folded over and secured to the arcuately cut side edges and then allowed to relax to gather in the pants or the diaper cover along the leg conforming side edges. In addition, segments of material have been cut out and secured along the arcuate edges in such a manner that they extend inwardly towards one another from the opposed arcuately cut side edges. These segments of fabric are typically referred to as "dams," in that they serve to help keep waste liquid and material from leaking out of the diaper in use.

SUMMARY OF THE INVENTION

In the present invention, arcuate leg conforming side edges and dams are provided in a protective garment without the cutting which has been required in manufacturing prior art protective garments. The body of the protective garment has opposed side portions which have been folded in towards one another, each along a generally arcuate fold line. The side portions are then secured to the remaining body generally along said arcuate fold lines, to thereby define arcuate leg conforming side edges along each said fold line and to provide a protective dam extending inwardly from said generally arcuate fold line along each side of said garment.

Preferably, though not essential to the broader aspects of this invention, the body comprises an absorbant pad, such that the protective garment is a diaper. It is believed that the diaper thus formed is the first diaper, as distinguished from a diaper cover or pants, having dams along its opposite side edges.

These and other aspects, objects and advantages of the invention will be more fully understood and appreciated by reference to the written specification and appended drawings.

DESCRIPTION OF THE PREFERRED EMBODIMENT

Figure 1:
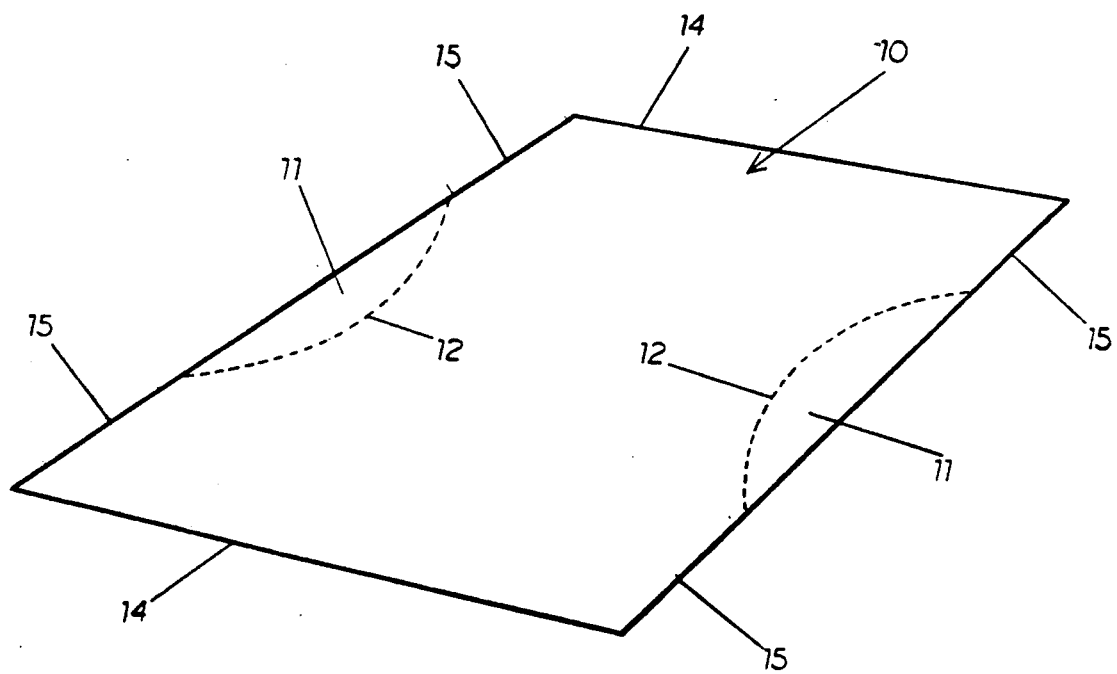
FIG. 1 is a perspective view of the body of the protective garment before forming, with the dashed lines being shown to indicate the fold lines.
Figure 2:
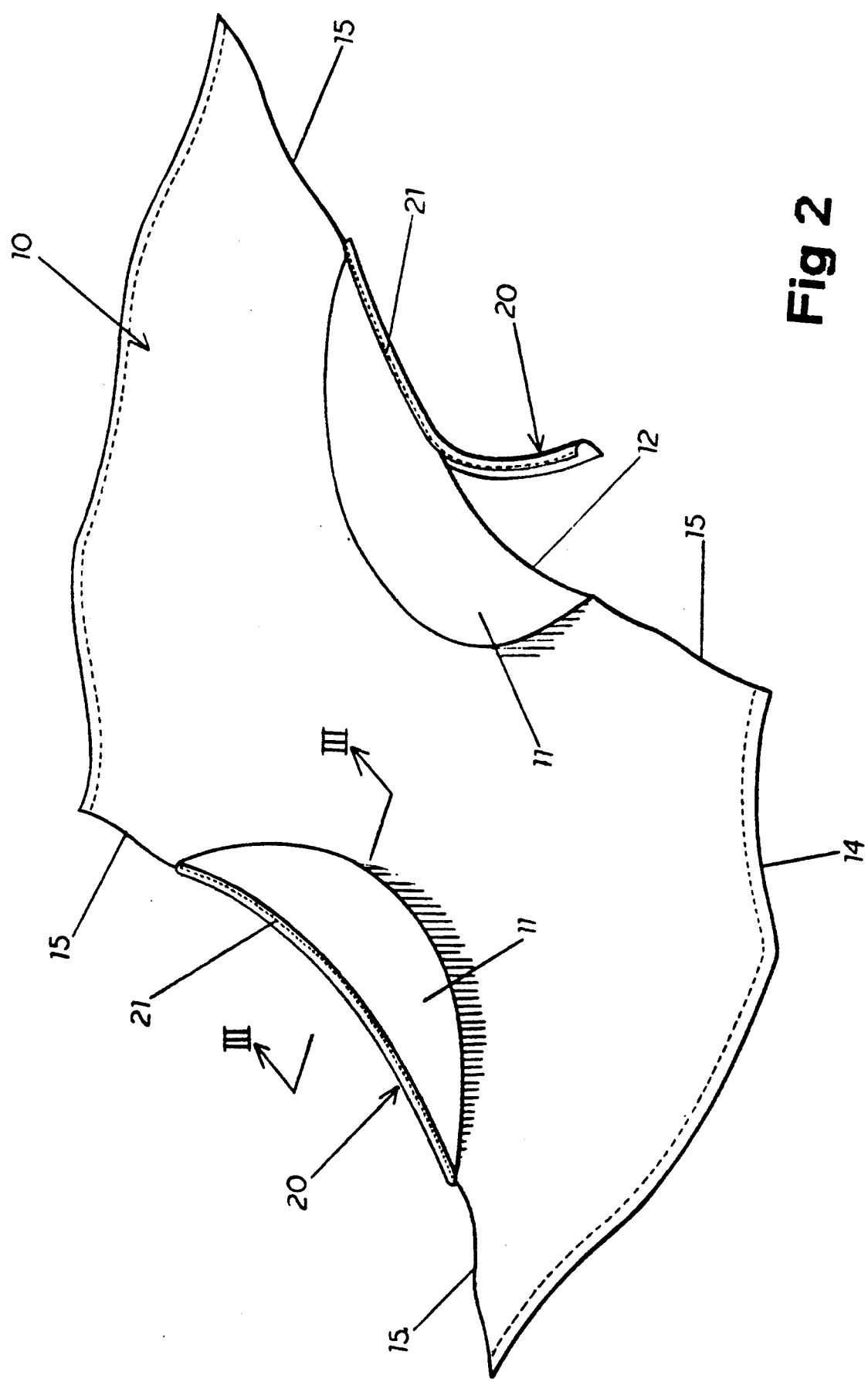
FIG. 2 is a perspective view of the protective garment after forming, with one of the elastic strips being shown partially peeled away from one of the folded edges.

In the preferred embodiment, protective garment body 10 includes side portions 11 which are folded inwardly towards one another along generally arcuate fold lines 12 (FIGS. 1 and 2). Strips of elastic material 20 in a stretched or at least partially stretched condition are folded over the folded edges of side portions 11 and are sewn thereto in an operation which simultaneously secures folded over side portions 11 to the remainder of body 10.

The material of which body 10 is made depends on the specific protective garment being produced. Materials typically used in any such specific garment would be appropriate. For example, diaper covers are often made of a fabric-backed or reinforced plastic material. A disposable diaper is typically made of a laminate of a plastic layer and a non-woven fabric absorbant pad. Reusable diapers are made of a cloth material, usually folded over some type of centrally located additional absorbant pad. The absorbant pad may be additional cloth or a non-woven fibrous material. Such materials can also be used in the present invention.

The side portions 11 of body 10 are folded over along arcuate fold lines 12 (FIGS. 1 and 2). The distance 15 from the beginning of each end of fold line 12 to each end 14 of body 10 may vary depending upon whether the garment is for a baby, a child or an adult. Distance 15 will typically be three to five inches in most applications, with an acceptable tolerance of plus or minus one-half inch.

Figure 3:
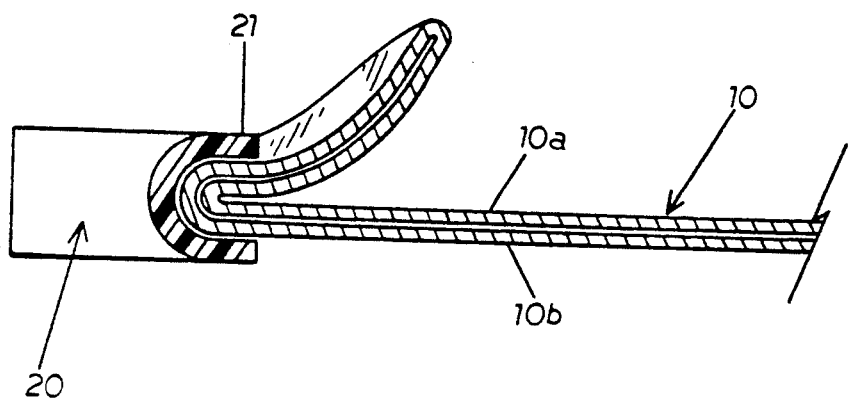
FIG. 3 is a fragmentary cross-sectional view taken along plane III—III of FIG. 2.

In the best mode contemplated, the protective garment will be a reusable cloth diaper and distance 15 will be three inches, plus or minus one-half inch. Body 10 comprises a woven cloth folded to define layers 10a and 10b (FIG. 3), the ends of which overlap in the center of the diaper. As is typical, the center of the diaper incorporates an additional absorbant padding material (not shown). The specific padding used is not at all pertinent to the present invention.

Any of a wide variety of elastic binding materials may be used. In the preferred embodiment, a three-quarter inch wide elastic binding is preferred.

Elastic binding 20 is secured to body 10 by a suitable securing means generally along fold lines 12. In the broader aspects of the invention, they do not have to lie precisely on fold lines 12. However, in the best mode contemplated, each elastic strip 20 is actually folded over fold line 12 and secured thereto (FIG. 2).

The manner of securement is not critical. The best mode contemplated is to sew the folded over elastic binding 20 to body 10 along fold line 12, as at seam line 21 (FIG. 2). Side portion 11 is thereby also secured to the remainder of body 10 along fold line 12. Stitch type 401 and seam type BSa are preferred, at twelve stitches per inch, plus or minus two. The preferred sewing thread is 50/2 spun polyester thread.

Each elastic binding 20 is secured along each fold line 12 in a somewhat stretched condition. The application of elastic binding strips in this manner is well-known to those skilled in the art. Conventional equipment is available for this operation. By applying elastic binding 20 in its stretched or at least partially stretched condition, the garment is contoured in a desirable manner when elastic binding 20 is relaxed, after it has been secured in place. This desirable contour makes the protective garment fit the wearer more snugly and neatly.

Once elastic binding 20 is sewn in place along seam 21, the ends are tacked and any excess binding 20 is trimmed. The preferred tacking stitch is type 304 at twenty-eight stitches per inch, plus or minus two. A suitable and preferred tacking thread is 70/2 spun polyester.

Of course, it is understood that the above is merely a preferred embodiment and that various changes and alterations can be made without departing from the spirit and broader aspects thereof, as set forth in the appended claims. The claims are to be interpreted in accordance with the principles of patent law, including without limitation the doctrine of equivalents.

The embodiments of the invention in which an exclusive property or privilege is claimed are defined as follows:

1. A garment for closely conforming contact with the lower torso of a mammal to absorb or otherwise contain body waste or exudate therefrom, comprising:
   a generally rectangular absorbent web;
   an arcuate fold formed along each of first and second opposite edges of said web through the thickness thereof and extending inwardly of the plane of said web, defining opposed containment flaps depending out of the plane of said web and further defining opposed, leg conforming side edges for anatomical conformity with the torso when the garment is disposed between the legs of a wearer; and
   elastic fixturing means secured proximate said arcuate folds for securing said containment flaps in a disposition toward the torso when the garment is in use, to contain within a central region of said web waste or exudate from said wearer;
   wherein said elastic fixturing means comprises an elastic strip disposed over the exterior of each of said arcuate folds in a stretched condition whereby, upon relaxation, said elastic fixturing means gathers said web.

2. A garment for closely conforming contact with the lower torso of a mammal to absorb or otherwise contain body waste or exudate therefrom, comprising:
   a web having a substantially planar configuration;
   an arcuate fold formed along each of first and second opposite edges of said web and extending inwardly of the plane of said web from said first and second opposite edges, defining first and second leg margins;
   first and second opposed side portions respectively proximate each of said folds and depending at said margins out of the plane of said web as continuous extensions thereof, defining means for containing the body waste within a central area of said web generally intermediate said folds;
   elastic fixturing means disposed proximate each of said folds for establishing the conformation of both (a) said leg margins and (b) said side portions;
   wherein said web comprises a substantially rectangular body and an absorbent material, whereby the garment is a diaper; and further
   wherein said elastic fixturing means comprises an elastic element disposed over the exterior of said arcuate fold.

3. A method of forming a garment for closely conforming contact with the lower torso of a mammal to absorb or otherwise contain body waste or exudate therefrom, comprising:
   (a) folding a substantially planar web along opposed arcuate fold lines extending inwardly of opposite edges of said web to define opposed containment flaps depending out of the plane of said web and further defining leg conforming side edges for anatomical conformity with the torso when the garment is disposed between the legs of a wearer; and
   (b) elastically securing said containment flaps along said arcuate fold lines in a disposition toward the torso when the garment is in use, to contain within a central region of said web waste or exudate from said wearer, wherein said web is gathered along said side edges.

4. The method of claim 3, wherein said securing step comprises securing said containment flaps in a disposition toward the torso when the garment is in use and securing an elastic strip over the exterior of said arcuate fold lines.

5. The method of claim 3, wherein said securing step comprises sewing said containment flaps to said web along said arcuate fold lines.

6. The method of claim 3, wherein said securing step further comprises placing an elastic strip over the exterior of said side edges and sewing said containment flaps to said web through said elastic strip.

* * * * *